United States Patent
Suzuki et al.

(10) Patent No.: US 7,293,874 B2
(45) Date of Patent: Nov. 13, 2007

(54) APPARATUS FOR MEASURING ANTERIOR OCULAR SEGMENT

(75) Inventors: Takayoshi Suzuki, Hamamatsu (JP); Takashi Mizuno, Hamamatsu (JP)

(73) Assignee: Kowa Company, Ltd., Aichi (JP)

( * ) Notice: Subject to any disclaimer, the term of this patent is extended or adjusted under 35 U.S.C. 154(b) by 587 days.

(21) Appl. No.: 10/850,313

(22) Filed: May 19, 2004

(65) Prior Publication Data
US 2005/0179867 A1 Aug. 18, 2005

(30) Foreign Application Priority Data
Feb. 13, 2004 (JP) ............... 2004-036784

(51) Int. Cl.
*A61B 3/14* (2006.01)
(52) U.S. Cl. ..................... 351/208; 351/206
(58) Field of Classification Search ............ 351/206, 351/208
See application file for complete search history.

(56) References Cited

U.S. PATENT DOCUMENTS

| | | | | |
|---|---|---|---|---|
| 5,757,462 A | * | 5/1998 | Nanjo ................. | 351/206 |
| 5,864,382 A | * | 1/1999 | Soya et al. .......... | 351/206 |
| 5,909,268 A | * | 6/1999 | Isogai et al. ........ | 351/208 |
| 2004/0183997 A1 | * | 9/2004 | Suzuki ................ | 351/208 |

FOREIGN PATENT DOCUMENTS

| | | |
|---|---|---|
| JP | 64-017623 | 1/1989 |
| JP | 02-082938 | 3/1990 |
| JP | 02-200236 | 8/1990 |
| JP | 2001-275979 | 10/1991 |
| JP | 03-264044 | 11/1991 |
| JP | 2002-017681 | 1/2002 |
| JP | 2003-144389 | * 5/2003 |

\* cited by examiner

*Primary Examiner*—Jordan M. Schwartz
(74) *Attorney, Agent, or Firm*—Knobbe, Martens, Olson & Bear LLP

(57) ABSTRACT

In an apparatus that measures an optical property of an eye to be examined (A) to irradiate laser beam and to receive scattered light of a laser beam by a measurement unit (3). In the apparatus, the position of the measurement unit (3) with respect to the eye (A) is adjusted relatively based on images of the eye (A), photographed from front and oblique direction, and displayed on a monitor fixed the back of the measurement unit (3). According to the apparatus, the optical properties of the anterior ocular segment can be measured with high reproducibility, and alignment is east to perform.

4 Claims, 11 Drawing Sheets

| N | BG | (%) | FLARE | WA |
|---|------|----|------|---|
| 1 | 14.7 | 1  | 17.0 |   |
| 2 | 14.1 | 0  | 16.9 | C |
| 3 | 26.3 | 33 | 10.0 | B |
| 4 | 14.4 | 0  | 18.0 |   |
| 5 | 15.4 | 3  | 17.2 |   |
| 6 | 30.8 | 0  | 17.1 | S |
| 7 | 18.7 | 1  | 19.1 |   |
| 8 | 17.5 | 0  | 19.3 |   |
|   | AV.  |    | 16.8 |   |
|   | S.D. |    | 2.9  |   |

APPARATUS FOR MEASURING ANTERIOR OCULAR SEGMENT

BACKGROUND OF THE INVENTION

1. Field of the Invention

The present invention relates to an apparatus for measuring an anterior ocular segment capable of quantifying, for example, a protein concentration in the aqueous humor of an eye to be examined by measuring optical properties of the anterior segment of an eyeball of a person to be examined. More particularly, the present invention relates to an apparatus for measuring an anterior ocular segment in which improvement has been made regarding the positional adjustment (alignment) between the eye to be examined and the measuring apparatus, the display of an anterior ocular segment, and the storage of measurement data.

2. Description of the Related Art

A protein concentration (flare) and a cell number density in an anterior ocular segment reflect a disease of various symptoms including a postoperative inflammation. To quantitatively measure the protein concentration and the cell number density is clinically important. As a method of quantitatively measuring the protein concentration and the cell number density, there has been known a method in which an anterior ocular segment of a person to be examined is irradiated with a laser beam from a laser beam source, scattered light of the laser beam in the anterior ocular segment is received by a light receiving unit and converted into an electrical signal, and optical properties of the anterior ocular segment are calculated from the electrical signal.

As a measuring apparatus used for such a measuring method, an ophthalmologic measurement apparatus is disclosed in JP 64-017623 A. The ophthalmologic measurement apparatus is provided with a light receiving unit for monitoring. A virtual image on the surface of a cornea, of scattered light of a laser beam irradiated to the eye to be examined and the scattered light of the laser beam are received by the light receiving unit for monitoring. The positional adjustment (alignment) of the laser beam source and the light receiving unit for monitoring is performed in accordance with a position of the virtual image and a position of the scattered light on the light receiving unit for monitoring.

As the measuring apparatus, an ophthalmologic measurement apparatus is disclosed in JP 02-082938 A. The ophthalmologic measurement apparatus includes: an anterior ocular segment observing optical system having an objective for observing the anterior ocular segment of the eye to be examined; and an alignment optical system for projecting an index light for alignment to the eye to be examined commonly using the objective.

As the measuring apparatus, an ophthalmologic measurement apparatus is disclosed in JP 02-200236 A. In the ophthalmologic measurement apparatus, indexes for fixing a line of sight of the eye to be examined are located symmetric about the optical axis of the eyeball such that a positional relationship between the optical axis of the eyeball of the eye to be examined and the optical axis of the laser beam irradiation optical system at the irradiation of the laser beam in the case of the left eye to be examined becomes the same as the positional relationship therebetween in the case of the right eye to be examined.

As the measuring apparatus, an ophthalmologic measurement apparatus is disclosed in JP 03-264044 A. In the ophthalmologic measurement apparatus, the eye to be examined is irradiated with, for example, the above-mentioned laser beam. A signal which is received by the light receiving unit is processed to exhibit an alignment state to a measuring person. While an alignment index is displayed on the exhibited alignment state, whether or not the alignment is appropriate is exhibited by changing a color or a blinking rate of the alignment index.

With respect to a technique related to the measuring apparatus, an image processing system is disclosed in JP 2002-017681 A. In the image processing system, the same identification information is provided to an ophthalmologic image which is photographed by, for example, an ophthalmologic image taking apparatus and image-taking conditional information which is inputted by an input device. The ophthalmologic image and the image-taking conditional information are transferred as information for taking image to the ophthalmologic image taking apparatus.

With respect to a technique related to the measuring apparatus, a system for taking an image of an eye to be examined is disclosed in JP 2001-275979 A. In the system for taking an image of an eye to be examined, an image of the eye to be examined, which was photographed, for example, in the past and in which a region is set in advance on the image, is recorded. In current photographing, a photographing condition of the eye to be examined is set based on information of the region on the recorded image.

In the above-mentioned measuring method, the positional adjustment (alignment) between the laser beam source and the light receiving unit and the eye to be examined is important in accurately measuring the anterior ocular segment. However, the measuring apparatuses have some problems in accurately measuring the anterior ocular segment.

One example of the ophthalmologic measurement apparatuses is an apparatus that performs the alignment while viewing the anterior ocular segment of the eye to be examined from an oblique direction through an eyepiece. With such an apparatus, it is hard to perform alignment because the measuring person does not face the person to be examined. In addition, because the observation is performed using the eyepiece in the apparatus, it causes inconvenience for the measuring person when performing the alignment. Further, because, the measurement results are likely to reflect a skill in operation of the measuring person, and therefore, it is hard to perform the anterior ocular segment measurement having high reproducibility.

Another example of the ophthalmologic measurement apparatuses is an apparatus in which the alignment index is not exhibited. In such an apparatus, even if the alignment is attempted using as a guide the virtual image resulting from the scattered light, reflected light, or the like on the anterior ocular segment, a suitable position is not exhibited, so that the alignment largely depends on the judgment of the measuring person. Therefore, it is hard to perform the anterior ocular segment measurement having high reproducibility using the apparatus.

When the techniques related to the ophthalmologic measuring apparatus are applied to the above-mentioned ophthalmologic measuring apparatuses, they are advantages in that previous measurement conditions and previous measurement results with respect to the same measuring person and previous measurement conditions and previous measurement results with respect to another measuring person can be utilized for further measurement and diagnosis. However, in some cases, alignment operations performed on each image and indexes used are different from one measuring person to another or even different for the same measuring person at different times. Therefore, even when the alignment is performed using such techniques, it is hard to perform the anterior ocular segment measurement having high reproducibility in some case.

In the above-mentioned ophthalmologic measuring apparatuses, when the measurement position is shifted, the intensity of reflected light and the intensity of scattered light on the anterior ocular segment change, and affect a background value and a signal value. Therefore, even when the same eye is measured plural times by the same measuring person at the same day, a variation in measurement results is caused in some cases. Thus, in order to accurately judge a change with the passage of time of the eye to be examined, it is desirable that the alignment having high reproducibility is accurately performed for the anterior ocular segment measurement.

SUMMARY OF THE INVENTION

An object of the present invention is to provide an apparatus for measuring an anterior ocular segment, capable of measuring biological properties of an anterior ocular segment with at least high-reproducibility.

Further, an object of the present invention is to provide an apparatus for measuring an anterior ocular segment in which alignment is more easily performed.

In the present invention, when an optical property of an anterior ocular segment is measured, a positional relationship between an eye to be examined and a measurement optical system is adjusted based on images of the anterior ocular segment obtained by photographing from at least two directions such as the front direction with respect to the eye to be examined and an oblique direction with respect to the eye to be examined.

the present invention is an apparatus for measuring an optical property of an anterior ocular segment of an eye of a person to be examined, which comprises a laser beam source that irradiates a laser beam to the anterior ocular segment of the eye to be examined from an oblique direction with respect to the eye to be examined, a light receiving unit that receives scattered light of the laser beam which is scattered in the anterior ocular segment and converts the scattered light into an electrical signal, and a calculation unit that calculates the optical property of the anterior ocular segment from the electrical signal, the apparatus further comprising:

a first light source that irradiates light to the eye to be examined from a front side with respect to the eye to be examined;

a first photographing means for photographing the eye to be examined from the front side;

a second light source that irradiates light to the eye to be examined from a first oblique direction with respect to the eye to be examined;

a second photographing means for photographing the eye to be examined from a second oblique direction with respect to the eye to be examined;

a position adjustment means for relatively adjusting each of positions of, the laser beam source, the light receiving unit, the first and second light sources, and the first and second photographing means with respect to a position of the eye to be examined;

a display unit that displays images obtained by the first and second photographing means; and a switching unit that switches an image signal transmitted from one of the first and second photographing means to the display unit in accordance with an on-and-off operation of one of the first and second light sources, in which the on-and-off operation of one of the first light source and the second light source and display on the display unit, of an image obtained by one of the first photographing means and the second photographing means are performed corresponding to each other, and the positions of the laser beam source and the light receiving unit are relatively adjusted with respect to the position of the eye to be examined based on a first virtual image and a second virtual image, the first virtual image is observed on an image of the eye to be examined, which is obtained by the first photographing means at irradiation of the light from the first light source, and the second virtual image is observed on an image of the eye to be examined, which is obtained by the second photographing means at irradiation of the light from the second light source.

In measuring apparatus of the present invention, the positions of the laser beam source and the light receiving unit, and the position of the eye to be examined are adjusted relatively from the two directions, the front direction and the oblique direction, with respect to the eye to be examined.

Therefore, each of distances, a distance between the laser beam source and the eye to be examined and a distance between the light receiving unit and the eye to be examined is easily adjusted to a predetermined value and each positional relationship of those in a horizontal direction and a vertical direction is easily adjusted to a predetermined relationship.

Thus, it is possible to improve the reproducibility of the adjustment of the positions of the laser beam source and the light receiving unit with respect to the position of the eye to be examined, so that the optical properties of the anterior ocular segment can be measured with high reproducibility.

The measuring apparatus in the present invention is an apparatus for measuring the optical properties of the anterior ocular segment and comprises: the laser beam source that irradiates the laser beam to the anterior ocular segment of the eye to be examined from the oblique direction with respect to the eye to be examined; the light receiving unit that receives the scattered light of the laser beam which is scattered in the anterior ocular segment and converts the scattered light into the electrical signal; and the calculation unit that calculates the optical property of the anterior ocular segment from the converted electrical signal. Such an optical system for measuring the anterior ocular segment and an information processing unit can be constructed as in a known apparatus for measuring an anterior ocular segment.

The measuring apparatus in the present invention comprises: the first light source that irradiates the light to the eye to be examined from the front side with respect to the eye to be examined; and the second light source that irradiates the light to the eye to be examined from the first oblique direction with respect to the eye to be examined.

The first and second light sources are not particularly limited as long as they are each a light source capable of forming a virtual image on the anterior ocular segment of the eye to be examined by irradiating the eye to be examined with light.

The first and second light sources may be the same type of light source or a different type of light source. As each of the first and second light sources, a device that irradiates infrared light such as a light emitting diode that generates infrared light is preferable to reduce a burden on the eye to be examined and to obtain a clear virtual image.

Note that "a virtual image" in the present invention indicates an optical image shown by the reflection on the cornea at a time when the eye to be examined is irradiated with light.

The measuring apparatus in the present invention comprises: the first photographing means for photographing the eye to be examined from the front side; and the second photographing means for photographing the eye to be examined from the second oblique direction with respect to the eye to be examined.

The first photographing means is not particularly limited as long as it is a photographing means capable of obtaining a virtual image formed in the eye to be examined (hereinafter the virtual image is also referred to as "the first virtual image") by light irradiation from the first light source.

The second photographing means is not particularly limited as long as it is a photographing means capable of obtaining a virtual image formed in the eye to be examined (hereinafter the virtual image is also referred to as "the second virtual image") by light irradiation from the second light source.

The first and second photographing means may be the same type of photographing means or a different type of photographing means. As each of the first and second photographing means, an image sensor such as a CCD image sensor is preferable to facilitate processing of the photographing image and structures of those.

In the present invention, in order to accurately perform the alignment with high reproducibility, it is preferable that the first photographing means is provided at a position relatively determined with respect to the first light source. This is because a displacement of the position of the first virtual image due to a deviation in positional relationship between the first photographing means and the first light source can be prevented. In order to perform the same, it is preferable that the second photographing means is provided at a position relatively determined with respect to the second light source.

In particular, it is preferable that the second photographing means and the second light source is in a positional relationship that an optical axis from the second light source to the eye to be examined and an axis from the eye to be examined to the second photographing means are perpendicular to each other.

The measuring apparatus in the present invention comprises the position adjustment means that relatively adjusts each of the positions of, the laser beam source, the light receiving unit, the first and second light sources, and the first and second photographing means with respect to the position of the eye to be examined.

The position adjustment means may be a means that separately adjusts the respective positions of, the laser beam source, the light receiving unit, the first and second light sources, and the first and second photographing means.

Alternatively, it may be a means that separately adjusts a position of a combination of the laser beam source and the light receiving unit, a position of a combination of the first light source and the first photographing means, and a position of a combination of the second light source and the second photographing means.

Alternatively, it may be a means that adjusts all positions of those sources units, and means with respect to the eye to be examined.

Alternatively, it may be a means that adjusts a position of the person to be examined or a position of the face of the person to be examined with respect to fixed sources, units, and means.

In order to perform accurate alignment by easy operation, it is preferable that the position adjustment means is a base which is relatively movable with respect to the eye to be examined, the base composed of the laser beam source, the light receiving unit, the first and second light sources, and the first and second photographing means.

The measuring apparatus in the present invention comprises the display unit that displays images obtained by the first and second photographing means. A general display device for displaying an image and information can be used for the display unit.

In order to accurately perform the alignment with high reproducibility, it is preferable that the display unit further displays suitable positions of the first and second virtual images. In the present invention, the suitable positions of the first and second virtual images change according to a measurement object and a measurement region. The suitable positions may be calculated as theoretical values or obtained from experiences. The suitable positions may be displayed using marks provided on a screen or using images shown on the screen.

In the present invention, it is preferable that the display unit is a display device, and the display unit is provided on the rear side of the first light source when an irradiation direction of light from the first light source is assumed to be the front side.

According to the structure, an inconvenience in the case where an eyepiece is used, that is, an inconvenience which is caused by extremely limiting the visual field of a measuring person at the time of alignment is eliminated.

In addition, according to the structure, the measuring person that performs the alignment is opposite to the person to be examined at the time of alignment, so that the measuring person further easily conducts the alignment operation.

The display device may be fixed rearward on the rear side of the first light source. Alternatively, the display device may be provided so as to be capable of being moved to the rear side of the first light source and supported by, for example, a flexible or pivotable support member.

The measuring apparatus in the present invention comprises the switching unit that switches one of the image signal transmitted from the first and second photographing means to the display unit in accordance with the on-and-off operation of one of the first and second light sources.

The switching unit causes the display unit to display the image obtained by the first photographing means in a state in which the first light source is on and causes the display unit to display the image obtained by the second photographing means instead of the image obtained by the first photographing means in a state in which the first light source is off and the second light source is on. A general switch for switching between signals can be used as the switching unit.

When the suitable positions of the first and second virtual images are shown in the image displayed on the display unit, in order to accurately perform the alignment with high reproducibility by easy operation, it is preferable that the switching unit switches a display of the suitable position of one of the first virtual image and the second virtual image in accordance with the on-and-off operation of one of the first and second light sources.

In the present invention, the on-and-off operation of one of the first light source and the second light sources and the display on the display unit, of the image obtained by one of the first photographing means and the second photographing means are performed corresponding to each other. Switching between the light sources and switching of the display on the screen can be performed by the switching unit.

In addition, in the present invention, the positions of the laser beam source and the light receiving unit and the position of the eye to be examined are relatively adjusted based on the first virtual image and the second virtual image. The adjustment can be performed by the position adjustment means.

The measuring apparatus in the present invention may further comprise a recording unit that records the quantity of light of one of the first and second light sources and the image of the eye to be examined, which is obtained by one of the first and second photographing means.

In order to accurately perform the alignment with high reproducibility, it is preferable that the measuring apparatus further comprises the recording unit because previous alignment information can be utilized for next alignment. A general storage for recording information can be used as the recording unit.

When the measuring apparatus comprises the recording unit, in order to accurately perform the alignment with high reproducibility, it is preferable that the calculation unit extracts the first and second virtual images from the image of the eye to be examined and causes the recording unit to record information of positions of the extracted virtual images on the image of the eye to be examined. The extraction of the virtual images and the determination of positions thereof in the image of the eye to be examined can be performed by known image processing.

Further, when the measuring apparatus in the present invention comprises the recording unit, it may further comprise an input means for inputting data from an outside to the calculation unit.

In such a case, in order to accurately perform the alignment with high reproducibility, to arrange stored measurement data for later utilization, and to utilize the arranged data, it is preferable that the calculation unit causes the recording unit to record the quantity of light of the first and second light sources, one of the image of the eye to be examined and information of the positions of the virtual images, and various data inputted by the input means, as being associated with one another.

As long as the various data inputted by the input means specify the person to be examined or the eye to be examined, they are not particularly limited. With respect to such data, there are, for example, an identification number of the person to be examined and right-and-left display data indicating whether the eye to be examined is a left eyeball or a right eyeball.

A commercial personal computer can be used for a part of or the entire recording unit, a part of or the entire calculation unit, and the input means.

When the position adjustment means is the base, information related to the measurement can be determined based on a position of the base. With respect to the information determined based on the position of the base, there are the right-and-left display data, information indicating that the person to be examined is at a position that alignment is allowed, and the like.

It is preferable to determine such information based on the position of the base because the alignment operation and the operation related to the alignment such as data input are facilitated.

It is preferable that the measuring apparatus in the present invention is constructed such that the second photographing means can obtain a real image resulting from scattered light of a laser beam, which is produced by irradiation of the laser beam from the laser beam source and the switching unit switches the image signal transmitted from one of the first and second photographing means to the display unit in accordance with one of an on-and-off operation of the first light source and on-and-off operations of the second light sources and the laser beam source. The structure can be realized as follows.

The second light source is disposed at a position for irradiating the eye to be examined with light at substantially the same angle as the laser beam. A light split means such as a half mirror or a holed mirror, which reflects or transmits a part of reflected light or a part of scattered light on the eye to be examined to the second photographing means, is disposed on an optical axis from the eye to be examined to the light receiving unit. The switching unit is constructed to further perform switching in accordance with an on-and-off operation of the laser beam source.

According to the structure, it is possible to relatively adjust the positions of the laser beam source and the light receiving unit and the position of the eye to be examined based on the real image in addition to the first and second virtual images.

In addition, according to the structure, the alignment using the laser beam is performed based on the image obtained by the second photographing means, so that an additional alignment optical system is not required. Therefore, it is preferable because the operationality of the alignment is improved by using a simple structure. In the present invention, in the case of the above-mentioned structure, it is preferable to display a suitable position of the real image on the display unit because the operationality of the alignment is improved by using a simple structure.

The measuring apparatus in the present invention can be used for various measurements related to optical properties of the anterior ocular segment, such as a protein concentration and a cell number density in an anterior ocular chamber, which are obtained from scattered light at a time when the eye to be examined is irradiated with the laser beam.

According to the present invention, in the apparatus that measures the optical properties of the anterior ocular segment, the positions of the laser beam source and the light receiving unit with respect to the position of the eye to be examined can be adjusted based on the two virtual images resulting from light irradiated from at least two directions. Therefore, the positions of the laser beam source and the light receiving unit with respect to the position of the eye to be examined can be adjusted to a predetermined positional relationship suitable for measurement at high precision as compared with the adjustment of positions based on a single virtual image. Thus, a variation in measurement is suppressed when the same eye to be examined is measured at the same day, so that data having higher reliability can be obtained in observation of processes such as pre-operation and post-operation.

According to the present invention, the positions of the laser beam source and the light receiving unit with respect to the position of the eye to be examined can be adjusted while observing the display unit. Therefore, those positions can be easily adjusted as compared with the case where an eyepiece is used.

In the present invention, when a device that irradiates infrared light is used as each of the first light source and the second light source, it is more effective in obtaining a clear virtual image and reducing a burden on the eye to be examined.

In the present invention, when the second photographing means obtains the real image resulting from the scattered light at a time when the eye to be examined is irradiated with the laser beam from the laser beam source, and the switching unit switches the image signal transmitted from one of the first and second photographing means to the display unit in accordance with the on-and-off operation of the first light source or the on-and-off operations of the second light sources and the laser light source, the on-and-off operation of the first light source or the on-and-off operations of the second light sources and the laser beam source and display on the display unit, of the image obtained by one of the first photographing means and the second photographing means are performed corresponding to each other. Also, the positions of the laser beam source and the light receiving unit with respect to the position of the eye to be examined are relatively adjusted based on the real image in addition to the first and second virtual images. Therefore, it is more effective in accurately performing the alignment with high reproducibility.

In the present invention, if suitable positions of the first and second virtual images are displayed on the display unit, it is more effective in accurately performing the alignment with high reproducibility. If a suitable position of the real image is further displayed on the display unit, it is still more effective.

In the present invention, if switching a display of the suitable positions of one of the first virtual image and the second virtual image is performed in accordance with the on-and-off operations of one of the first and second light sources, it is more effective in easily performing accurate alignment with high reproducibility. If switching a display of the suitable position of the real image is performed together with the switching a display of the suitable position of the first virtual image and the second virtual image, it is still more effective.

In the present invention, if data related to alignment and measurement, such as an alignment condition, a measurement condition, and a measurement result are recorded in the recording unit, it is more effective performing accurate alignment with high reproducibility. If data related to the eye to be examined and the person to be examined is further recorded in the recording unit as associated with the data related to measurement, it is useful to utilize the data related to measurement, which is recorded in the recording unit, so that it is further more effective.

In the present invention, when predetermined data is automatically determined based on a position of a constitution element of the measuring apparatus, such as the position of the base, it is more effective in easily performing accurate alignment with high reproducibility.

In the present invention, when a display device is used as the display unit and provided on the rear side of the first light source, the inconvenience to an alignment operation, which is caused by limiting the visual field of a measuring person, and the inconvenience to an alignment operation, which is caused by a difference between a viewing direction of the measuring person and an operating direction that the measurement person is going to operate for alignment, are eliminated. Therefore, the operationality of the alignment can be more easily improved.

DESCRIPTION OF THE PREFERRED EMBODIMENT

Hereinafter, an embodiment of the present invention will be described.

Figure 1:
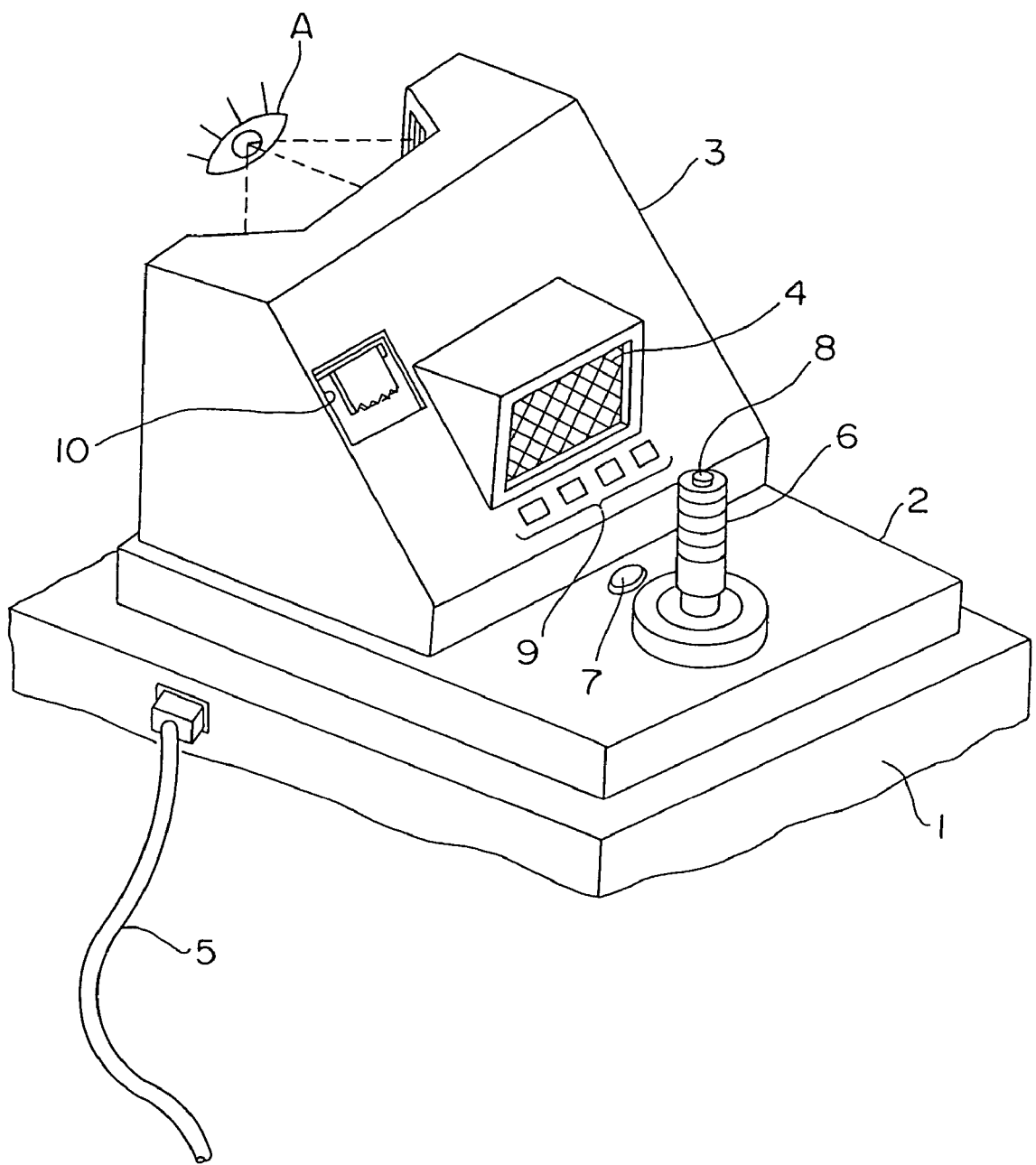
FIG. 1 is an outline view showing a measuring apparatus according to an embodiment of the present invention.

As shown in FIG. 1, an apparatus for measuring an anterior ocular segment according to this embodiment comprises a fixed base 1, a base 2 which is provided so as to be movable on the fixed base 1, a measurement unit 3 fixed onto the base 2, and a monitor 4 as a display unit, which is fixed to the measurement unit 3.

The fixed base 1 is connected with a communication cable 5 connected with a personal computer. A base position detector (not shown in FIG. 1) that detects a position of the base 2, a support stand that supports the face of a person to be examined (not shown), and the like are provided in the fixed base 1. A joystick 6 as an operation unit for moving the base 2 and performing various operations for alignment and a screen switching button 7 for instructing the switching among images displayed on the monitor 4 are provided on the base 2. A measurement button 8 is provided at the top portion of the joystick 6.

The measurement unit 3 comprises, in addition to the monitor 4, four functional buttons 9, a printer which is not shown, an ejection port 10 for ejecting a sheet of a measurement result which is printed by the printer, an alignment and measurement optical system, and an alignment and measurement control system. Note that the monitor 4 is fixed onto the rear surface of the measurement unit 3 whose front surface is opposite to a person to be examined in a state in which a screen surface is reversed to the person to be examined such that a measuring person can view an image with a state in which the measuring person is opposite to the person to be examined.

Figure 2:
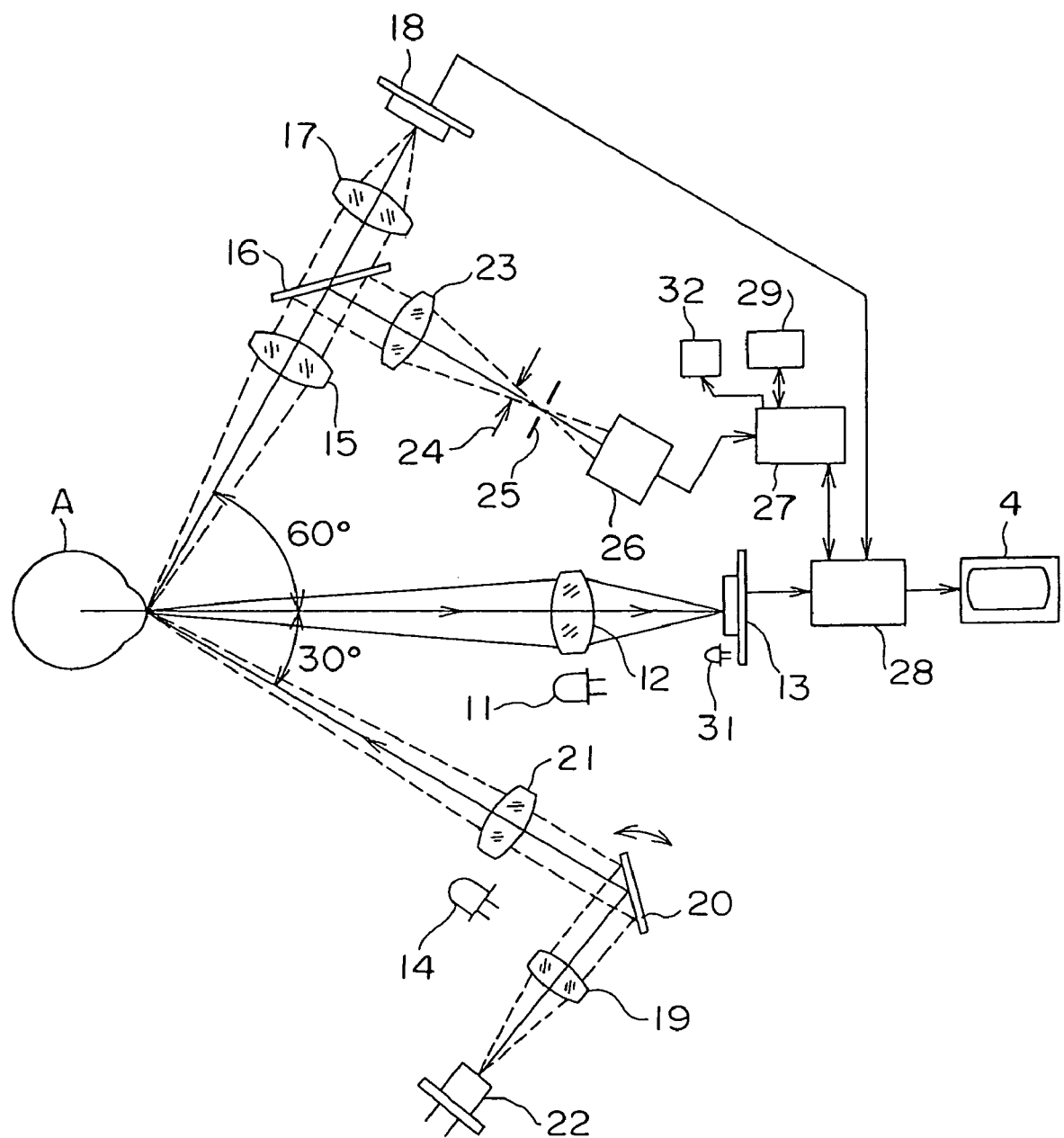
FIG. 2 is a diagram showing a structure of an optical system of the measuring apparatus shown in FIG. 1.

As shown in FIG. 2, the alignment and measurement optical system comprises, an infrared LED 11 as a first light source, a CCD 13 as a first photographing means, an infrared LED 14 as a second light source, a CCD 18 as a second photographing means, a semiconductor laser 22 as a laser beam source, and a high sensitive light receiving element 26 as a light receiving unit.

The infrared LED 11 irradiates light from the front side to an eye to be examined "A". The CCD 13 photographs the eye to be examined "A" from the front side through a camera lens 12. The infrared LED 14 irradiates light to the eye to be examined "A" from an oblique direction at 30° with respect to the optical axis of the eye to be examined "A" (first oblique direction).

The CCD 18 is located on an opposite side of the infrared LED 14 with respect to the optical axis of the eye to be examined "A" and photographs the eye to be examined "A" from an oblique direction at 60° with respect to the optical axis of the eye to be examined "A" (second oblique direction) through an objective 15, a half mirror 16, and a camera lens 17.

The semiconductor laser 22 irradiates a laser beam to the eye to be examined "A" from the oblique direction at 30° with respect to the optical axis of the eye to be examined "A" through a collimating lens 19, a galvanomirror 20 which can pivot, and a projection lens 21 that limits a beam to the eye to be examined "A".

The high sensitive light receiving element 26 receives scattered light of the laser beam on the eye to be examined "A" through the objective 15, the half mirror 16, a light receiving lens 23, a shutter 24, and a light receiving mask 25.

The half mirror 16 is a mirror that permeates a part of light which reflected or scattered to the oblique direction at 60° with respect to the optical axis of the eye to be examined "A" without reflection and reflects the remaining part thereof to the light receiving lens 23. In this embodiment, a holed mirror may be used instead of the half mirror 16.

The light receiving lens 23 is a lens that limits light reflected on the half mirror 16 to the light receiving mask 25.

The high sensitive light receiving element 26 is a photoelectric converter that generates an electrical signal according to the received light.

Figure 3:
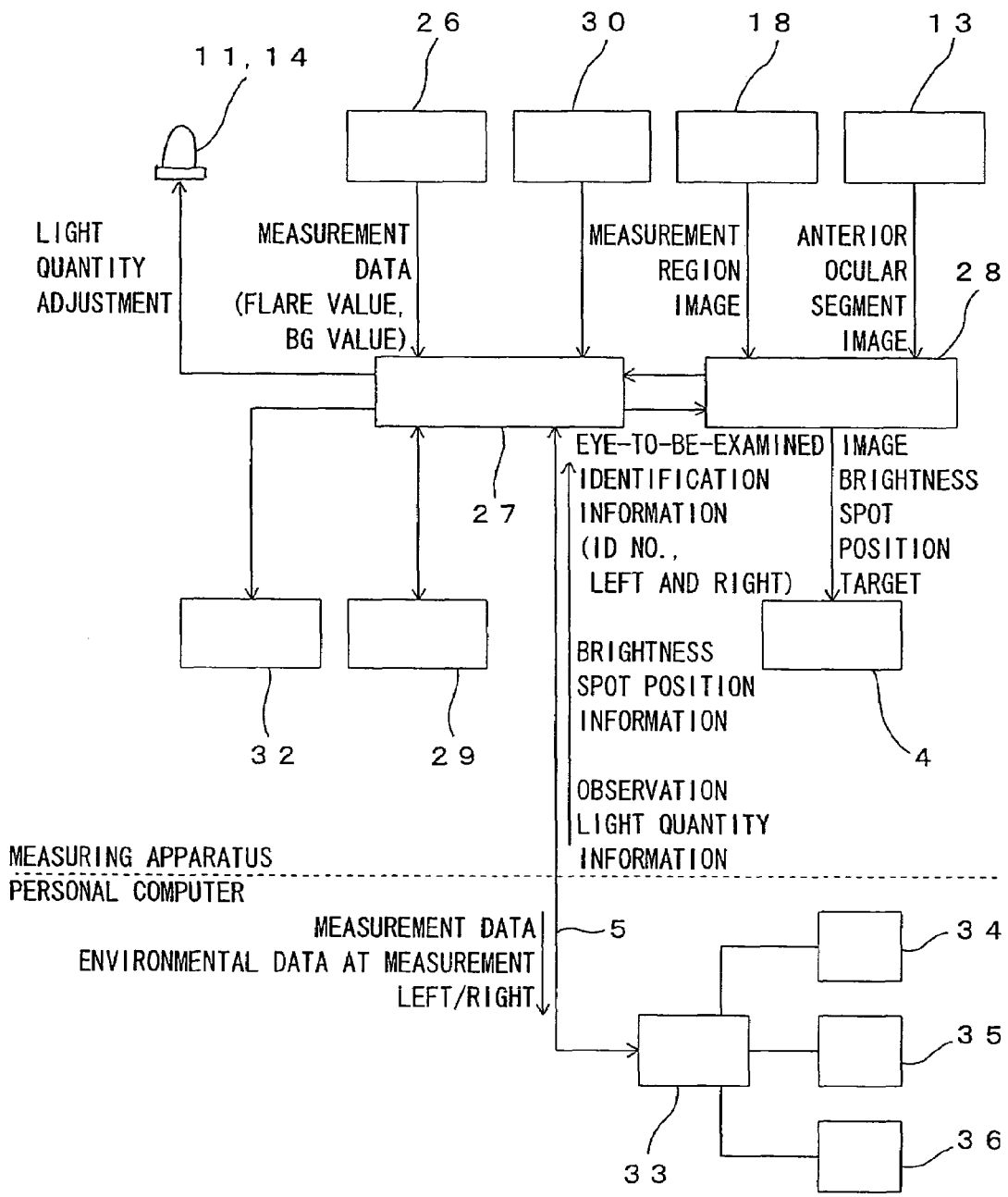
FIG. 3 is a block diagram showing a structure of a control system of the measuring apparatus shown in FIG. 1.

As shown in FIGS. 2 and 3, the alignment and measurement control system comprises a calculation unit 27, a switching unit 28, and a main body memory 29 as a recording unit.

The calculation unit 27 is connected with the high sensitive light receiving element 26. The calculation unit 27 calculates optical properties of the anterior ocular segment from the electrical signal outputted from the high sensitive light receiving element 26.

The switching unit 28 is connected with the CCDs 13 and 18 and the calculation unit 27 and switches an image signal outputted from one of the CCD 13 and 18 to the monitor 4 in accordance with the on/off of the infrared LEDs 11 and 14. The main body memory 29 is connected with the calculation unit 27.

In addition to those, the calculation unit 27 is connected with the infrared LEDs 11 and 14, a base position detector 30, and the like. The switching unit 28 is connected with the monitor 4.

The measurement unit 3 further comprises a fixation lamp 31 for fixing a line of sight of the eye to be examined and a printer 32 that prints a sheet ejected from the ejection port 10.

The communication cable 5 is connected with an external personal computer 33. The personal computer 33 is connected with an external printer 34, an external monitor 35, and a keyboard 36 as an input means.

Figure 4:
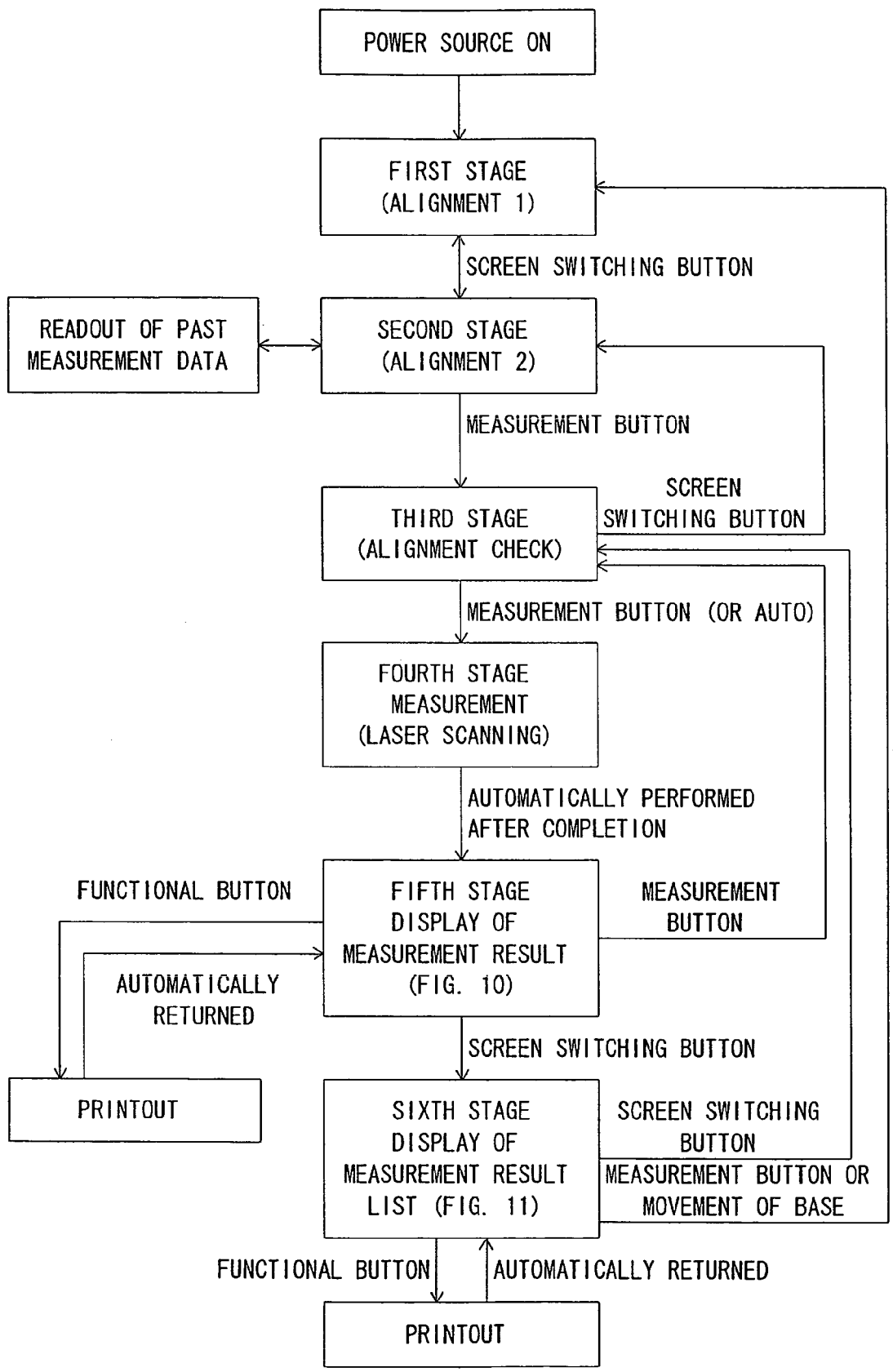
FIG. 4 is a flow chart showing all of the measurement performed by the measuring apparatus shown in FIG. 1.

A method of measuring the optical properties of the anterior ocular segment using the above-mentioned apparatus for measuring an anterior ocular segment will be described below. FIG. 4 is a flow chart showing all of the operation in the method.

First, a power source of the measuring apparatus is turned on. A face of the person to be examined is placed on the support stand. When the base 2 is moved to the outside of a predetermined area (for example, when it is moved to the person side), the movement of the base 2 is detected by the base position detector.

<First Stage (Alignment 1)>

In the first stage, the eye to be examined, which is irradiated with light from the front side is photographed from the front side. An image of the eye to be examined is displayed on the display unit. Positions of the laser beam source and the light receiving unit are relatively adjusted with respect to a position of the eye to be examined based on a position of a first virtual image displayed on the display unit. A suitable position of the first virtual image is displayed on the display unit and the position of the first virtual image is adjusted based on the suitable position.

Figure 5:
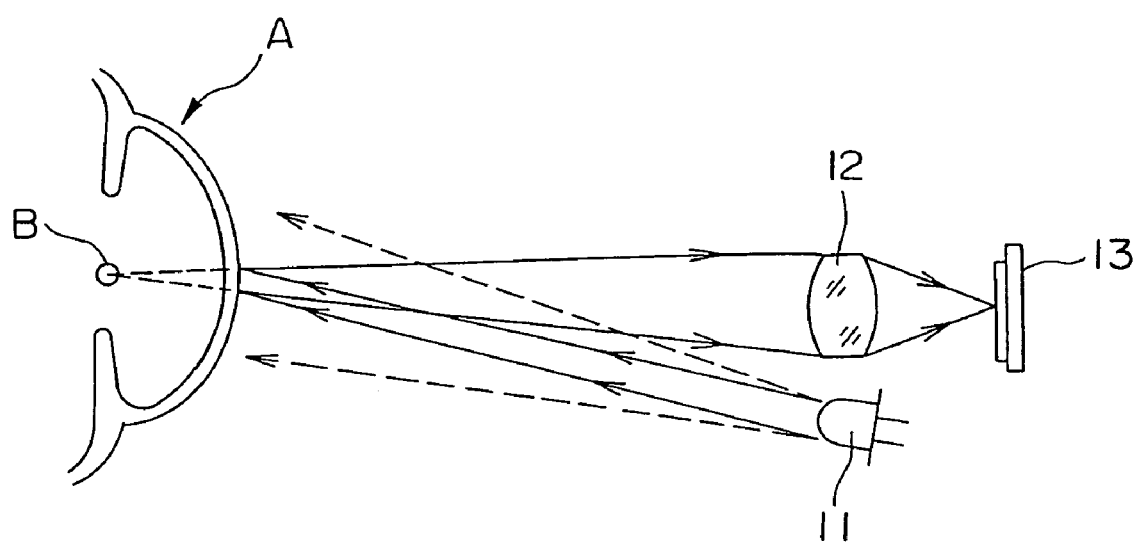
FIG. 5 is a diagram showing an optical system in a first stage shown in FIG. 4.

When the movement of the base 2 is detected by the base position detector, the calculation unit determines that the first stage of the alignment starts and causes the infrared LED 11 and the fixation lamp 31 to be turned on. Therefore, the line of sight of the eye to be examined is fixed and then the anterior ocular segment of the eye to be examined is irradiated with infrared light. The first virtual image is shown on the anterior ocular segment due to the irradiation of the infrared light. In addition, the image photographed by the CCD 13 is displayed on the monitor 4 due to the lighting of the infrared LED 11. FIG. 5 shows the alignment optical system using the infrared LED 11. Reflected light on the anterior ocular segment transmits through the camera lens 12. At this time, a lens barrel (lens holder) of the camera lens becomes an aperture diaphragm. Note that the infrared LED 11 is used as not only a light source for showing the first virtual image but also an illumination source for illuminating an iris.

After the lighting of the infrared LED 11, while the anterior ocular segment is observed by the CCD 13, a positional relationship between the eye to be examined and the measurement unit 3 is adjusted based on the position of the first virtual image displayed on the monitor 4. The adjustment is performed by operating the joystick 6 to move the base 2. Whether a distance relationship between the measurement unit 3 and the eye to be examined is good or bad can be determined by whether or not the first virtual image is observed as a brightness spot on the monitor 4 or whether or not the contour of a pupil and the pattern of an iris in the monitor 4 are clear.

Figure 6:
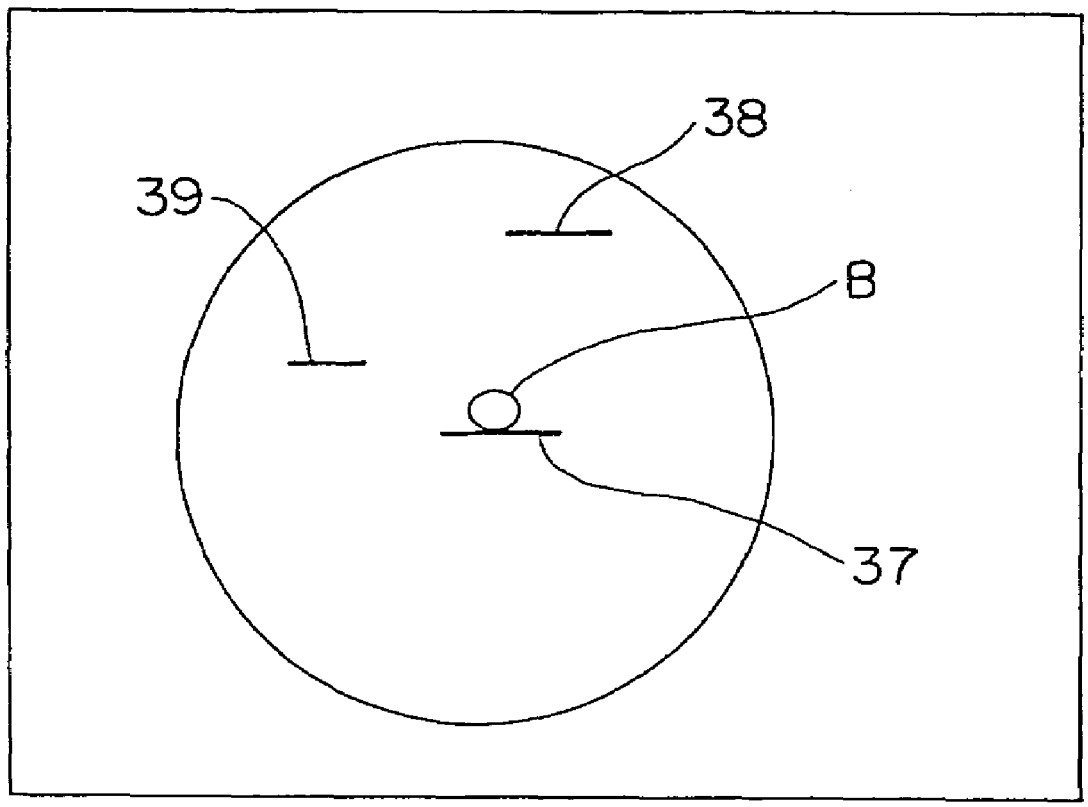
FIG. 6 is a drawing showing an example of a screen of a monitor 4 that displays a photographed front image of an eye to be examined in the first stage shown in FIG. 4.

As shown in FIG. 6, on the monitor 4, each of marks 37 to 39 is provided at each of the suitable positions of the first virtual image, a second virtual image, and a real image resulting from the scattered light of the laser. The joystick 6 is operated to move the base 2 such that the brightness spot (first virtual image "B") is displayed at a predetermined position corresponding the mark 37 (position overlapped with the mark 37 or its vicinities) provided on the monitor 4. After the measuring person judges that the adjustment of the positional relationship between the eye to be examined and the measurement unit 3 based on the first virtual image is completed, the measuring person presses the screen switching button 7.

<Second Stage (Alignment 2)>

In the second stage, the light source that illuminates the eye to be examined is switched from the light source located on the front side to the light source located in the first oblique direction. The photographing of the eye to be examined is changed from the front photographing to the photographing performed from the second oblique direction. The eye to be examined which is irradiated with light from the first oblique direction with respect to the eye to be examined is photographed from the second oblique direction with respect to the eye to be examined. An image of the eye to be examined is displayed on the display unit. The positions of the laser beam source and the light receiving unit are relatively adjusted with respect to the position of the eye to be examined based on a position of a second virtual image displayed on the display unit.

In addition, in the second stage, the eye to be examined which is irradiated with a laser beam is photographed from the second oblique direction with respect to the eye to be examined. An image of the eye to be examined is displayed on the display unit. The positions of the laser beam source and the light receiving unit are relatively adjusted with respect to the position of the eye to be examined based on a position of a real image resulting from scattered light of the laser beam, which is displayed on the display unit.

In the second stage, suitable positions of the second virtual image and the real image are displayed on the display unit and the positions of the second virtual image and the real image are adjusted based on the suitable positions of those.

Figure 7:
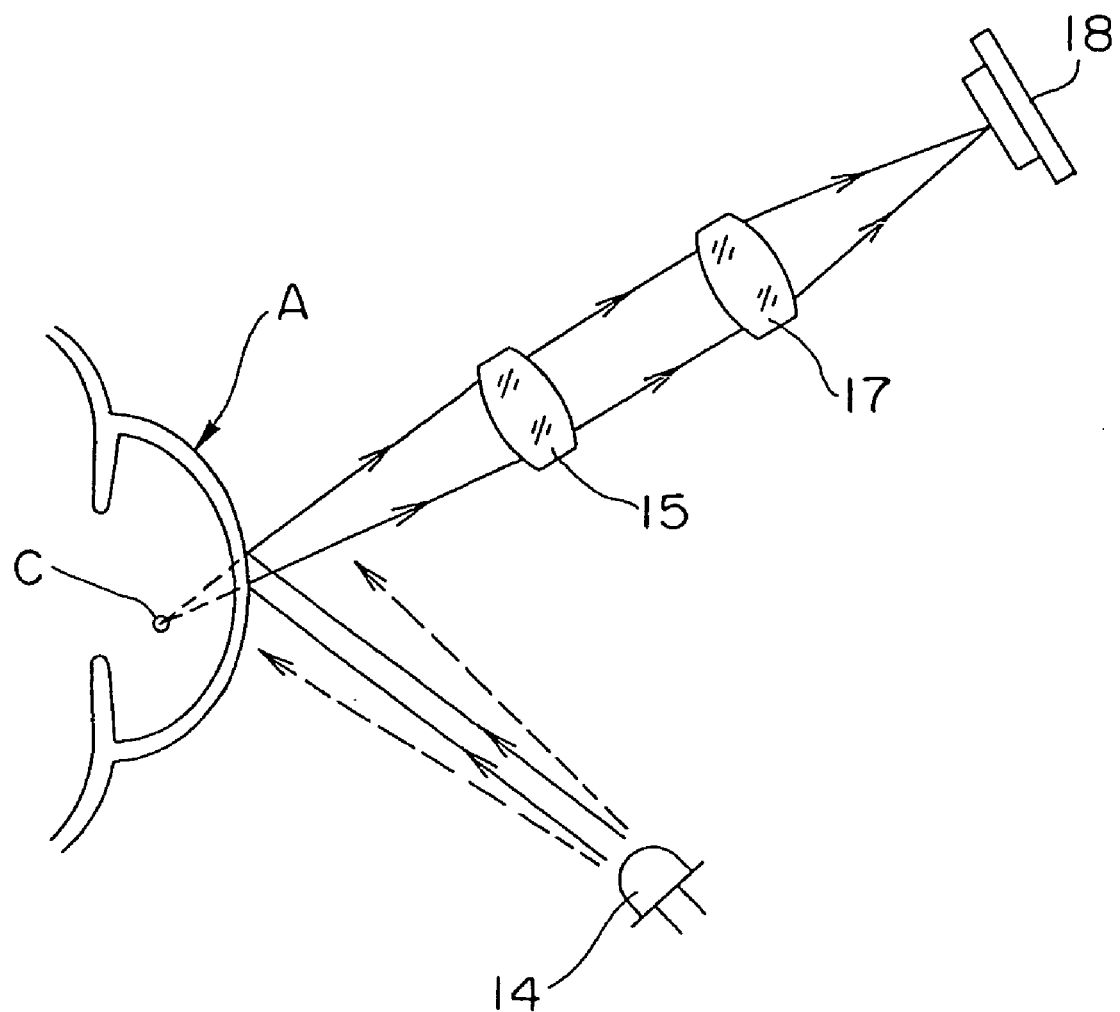
FIG. 7 is a diagram showing an optical system for alignment in a second stage shown in FIG. 4.

When the screen switching button 7 is pressed, the infrared LED 11 is turned off and the infrared LED 14 is turned on. The image sent to the monitor 4 is switched from the image signal outputted from the CCD13 to the image signal outputted from the CCD 18 by the switching unit 28. FIG. 7 shows the alignment optical system using the infrared LED 14. As in the infrared LED 11, the infrared LED 14 is used as not only a light source for showing the second virtual image but also an illumination source for illuminating the iris.

Figure 8:
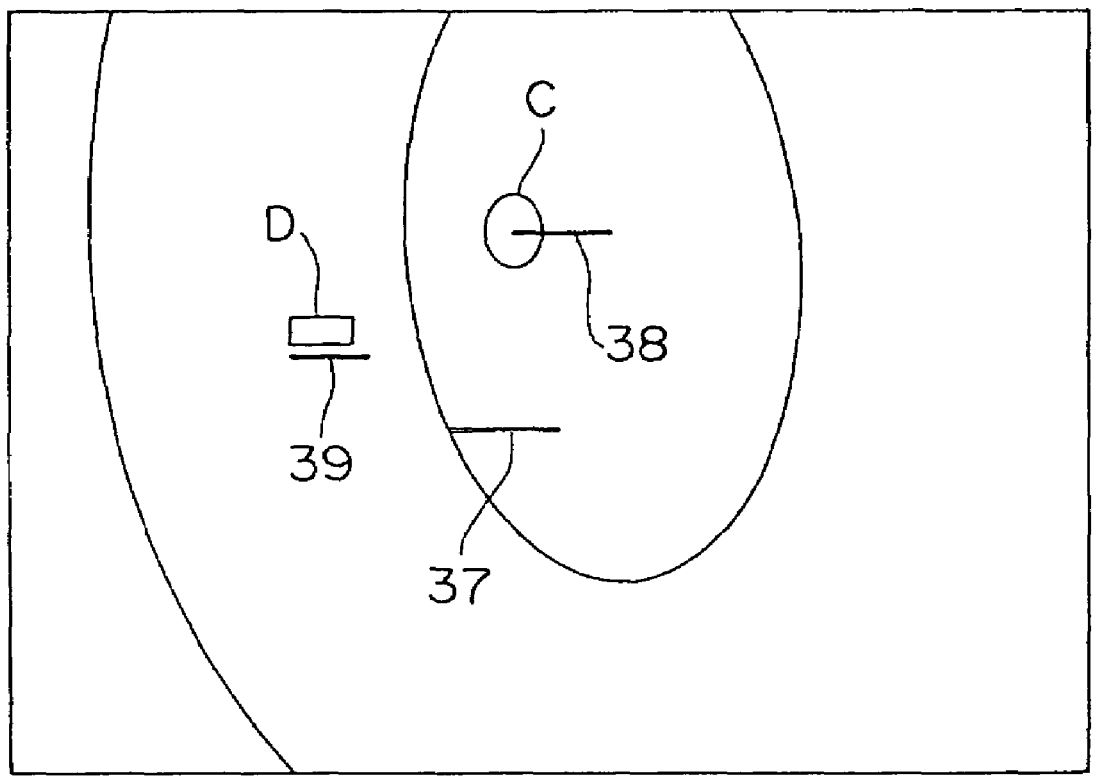
FIG. 8 is a drawing showing an example of the screen of the monitor 4 that displays an image of the eye to be examined which is photographed at an angle of 60° with respect to the eye to be examined in the second stage shown in FIG. 4.

As shown in FIG. 8, the image photographed by the CCD 18 is displayed on the monitor 4. A laser beam is irradiated from the semiconductor laser 22. Therefore, a second virtual image "C" produced by the infrared LED 14 and a real image "D" resulting from the light scattered on the cornea by the irradiation of the laser beam are displayed as brightness spots on the monitor 4. The base 2 is moved by the joystick 6 so as to display the second virtual image "C" and the real image "D" at predetermined positions corresponding to the marks 38 and 39. After the measuring person judges that the adjustment of the positional relationship between the eye to be examined and the measurement unit 3 based on the second virtual image "C" and the real image "D" is completed, the measuring person presses the measurement button 8.

Note that, in the above-mentioned first and second stages, when data related to the measurement of the same eye of the same person to be examined, which is performed in the past is stored, the designated functional button 9 is operated. Therefore, the quantity of light of the infrared LEDs 11 and 14, the quantity of light of the semiconductor laser 22, and the position of the marks 37 to 39 on the monitor 4 are set based on the stored data. When no data related to the measurement of the same eye is stored, for example, the marks 37 to 39 are provided to the positions theoretically calculated as initial values. Then, the above-mentioned first and second stages are performed.

When the screen switching button 7 is pressed instead of the measurement button 8 after the completion of the second stage, the lighting infrared LED and the screen displayed on the monitor 4 are switched to those in the first stage. Therefore, the first stage and the second stage may be repeated plural times.

<Third Stage (Check of Alignment)>

Figure 9:
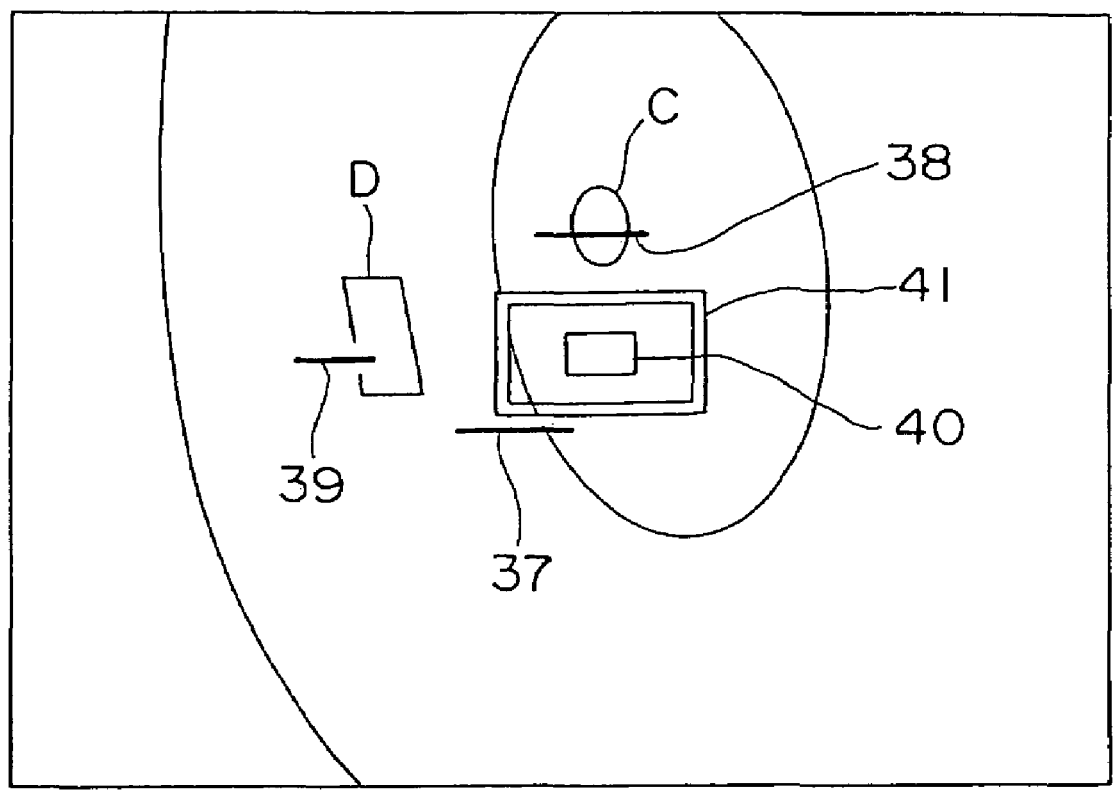
FIG. 9 is a drawing showing an example of the screen of the monitor 4 in a third stage shown in FIG. 4.

When the measurement button 8 is pressed, the calculation unit 27 causes the monitor 4 to display a measurement window 40 as shown in FIG. 9 through the switching unit 28. The measurement window 40 indicates a light receiving area of the high sensitive light receiving element 26, which is determined according to the aperture width of the light receiving mask 25. After the measurement window 40 is displayed, the calculation unit 27 causes the galvanomirror 20 to pivot. Therefore, a region within a frame 41 in FIG. 9 including the measurement window 40 is scanned with a laser beam and a background value is measured by the high sensitive light receiving element 26. The calculation unit 27 determines whether the alignment is good or bad according to a difference of background value between the outside and the inside of the measurement window 40 and magnitudes thereof. When the calculation unit 27 determines the alignment is good, for example, a blinking rate or a display color of the measurement window 40 is changed. Thus, the measuring person can confirm that the measuring apparatus is in a measurable state.

<Fourth Stage (Measurement)>

After the check of the alignment, the measurement of the optical properties of the anterior ocular segment is performed. Note that, immediately before the actual measurement, the calculation unit 27 causes the main body memory 29 to record alignment information such as the quantity of light of the infrared LEDs 11 and 14 and the positions of the brightness spots displayed on the monitor 4 at the completion of the third stage.

The measurement may be automatically or manually started. With respect to a mode capable of starting the measurement by any of automatic and manual operations, there are an automatic mode, a semiautomatic mode, and a manual mode.

In the automatic mode, when the calculation unit 27 determines that the alignment is sufficiently good, the measurement automatically starts without any operation. In this case, it is unnecessary to perform manual operation pressing the measurement button 8 or the like.

In the semiautomatic mode, when the calculation unit 27 determines that the alignment is sufficiently good and the measuring person presses the measurement button 8, the measurement starts. In this case, the measuring person can start the measurement with reference to a signal indicating good alignment, such as the blinking rate or the display color of the measurement window 40.

In the manual mode, regardless of the determination of the calculation unit 27, the measuring person presses the measurement 8 at a suitable timing with reference to the signal indicating good alignment, thereby starting the measurement.

In any mode, the measurement is performed one time.

<Fifth Stage (Display of Measurement Result)>

Figures 10, 11:
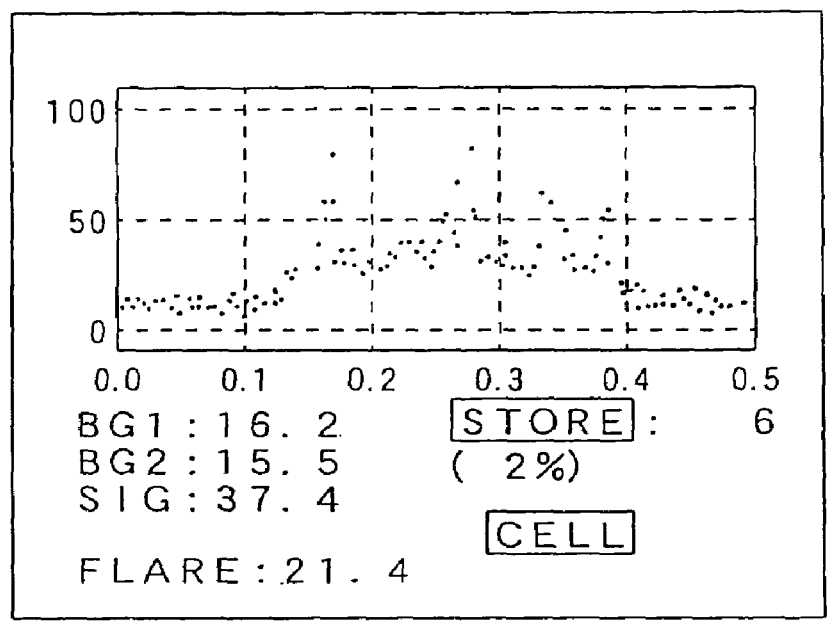
FIG. 10 is a drawing showing an example of a measurement result displayed in a fifth stage shown in FIG. 4.
FIG. 11 is a drawing showing an example of a list of a measurement result displayed in a sixth stage shown in FIG. 4.

In each mode, after the measurement is completed, a measurement result is recorded in the main body memory 29. The measurement result as shown in FIG. 10 is displayed on the monitor 4. When the designated functional button 9 is pressed with a state in which the measurement result is displayed on the monitor 4, the measurement result as shown in FIG. 10 is printed by the printer 32 and a printed sheet is ejected from the ejection port 10. When the measurement button 8 is pressed, the operation returns to the third stage, so that the measurement can be repeated. The measurement of the optical properties of the anterior ocular segment is repeated plural times if necessary.

<Sixth Stage (Display of Measurement Result List)>

When the screen switching button 7 is pressed after the measurement is performed one time or plural times, a table indicating a list of numerical values of the measurement result as shown in FIG. 11 is displayed on the monitor 4. In addition, the fixation lamp 31 is turned off. When the designated functional button 9 is pressed with a state in which the measurement result is displayed on the monitor 4, the measurement result as shown in FIG. 11 is printed by the printer 32 and a printed sheet is ejected from the ejection port 10. In addition, when the designated functional button 9 is pressed with a state in which the list of the measurement result is displayed on the monitor 4, the data of the measurement result is sent to the personal computer 33.

Next, a screen for confirming whether or not the alignment information in the fourth stage is recorded together with the data of the measurement result is displayed on the monitor 4. Whether or not the recording is necessary is specified by operating the functional button 9. When nothing is specified, the alignment information is not recorded and only the data of the measurement result is recorded in the main body memory 29.

Figure 12:
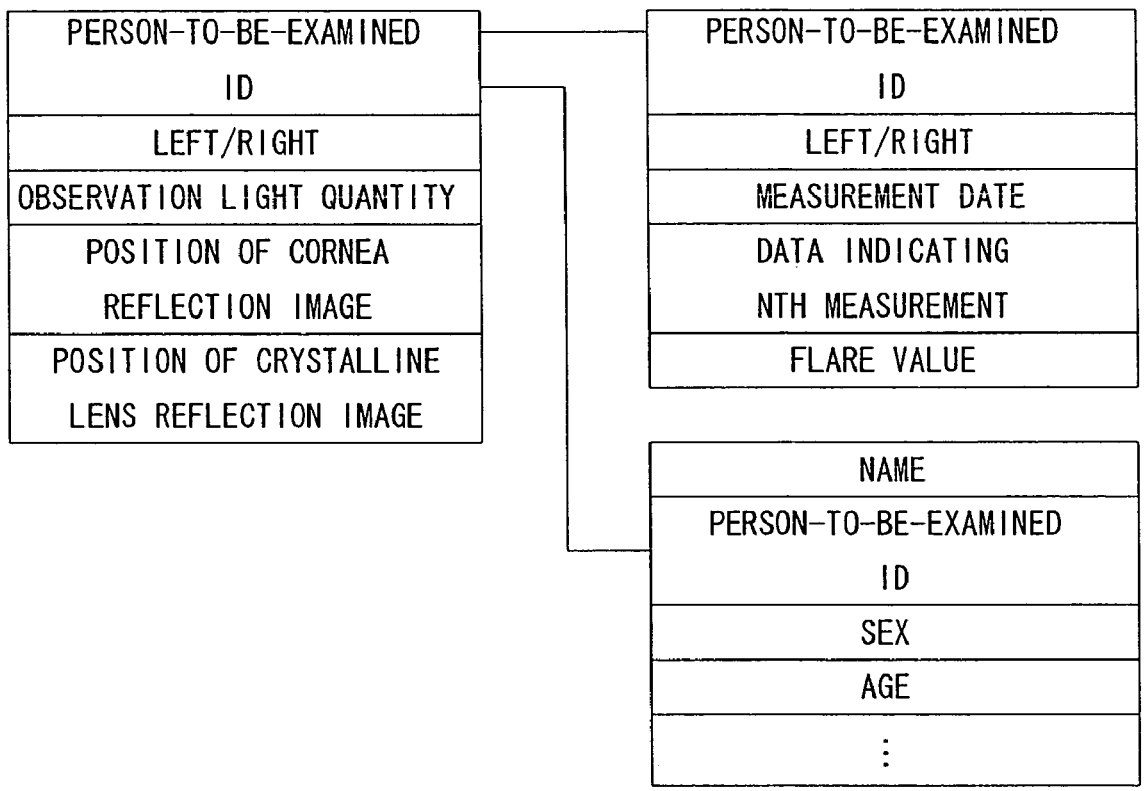
FIG. 12 is a diagram showing an example of data related to alignment and data related to a person to be examined and an eye to be examined, which are recorded in the sixth stage shown in FIG. 4, and a relation between those.

When it is specified that the alignment information is recorded together with the data of the measurement result, the data of the measurement result, the data related to the alignment, and the data related to the person to be examined and the eye to be examined are recorded in the main body memory 29 as being associated with one another. The data related to the alignment includes the quantity of light of the infrared LEDs 11 and 14 which is recorded in the measurement, and the respective positions and brightnesses of, a cornea reflection image, a crystalline lens reflection image, a laser spot, a laser reflection image on cornea, a laser reflection image on crystalline lens, and the like on an anterior ocular segment image which is displayed on the monitor 4, which are obtained by the extraction using image processing. The data related to the person to be examined and the eye to be examined includes a person-to-be-examined ID for identifying the individual person to be examined and right and left eye data and the like (see FIG. 12). The data recorded in the main body memory 29 can be sent to the personal computer 33 by operating the functional button 9, so that the data can be stored in the personal computer 33.

When the base 2 is largely moved or the measurement button 8 is pressed, the display content of the monitor 4 is returned to that in the first stage. At this time, the recording contents of the main body memory 29 are deleted. Note that, in order to prevent a deletion error, a message for confirming whether or not the deletion of the recording contents is desired is displayed on the monitor 4. When the designated functional button 9 is pressed in this time, the data in the main body memory 29 is deleted. When the screen switching button 7 is pressed, the display content of the monitor 4 is returned to that in the third stage and then the same eye to be examined is measured. In this case, the data in the main body memory 29 is not deleted.

According to this embodiment, the position of the measurement unit 3 with respect to the position of the eye to be examined "A" are adjusted based on the first virtual image produced by irradiating the eye to be examined "A" with the light from the front side and the second virtual image produced by irradiating the eye to be examined "A" with the light from the oblique direction. Therefore, the positional adjustment is performed from the two directions, so that it is possible to perform the alignment having higher precision than a conventional measuring apparatus. Thus, the optical properties of the anterior ocular segment can be measured with high reproducibility.

In this embodiment, the monitor 4 is provided on the rear surface of the measurement unit 3, that is, on the rear side of the infrared LED 11 when the irradiation direction of the infrared light from the infrared LED 11 is assumed to be the front side. Therefore, the visual field of the measuring person during the alignment does not become narrower. In addition, because the measuring person performs alignment with in a state in which the measuring person faces the person to be examined, the measuring person is unlikely to mislead the direction of the alignment operation. Therefore, the inconvenience to the alignment operation, which is caused by limiting the visual field of the measuring person and the inconvenience to the alignment operation, which is caused by a difference between a viewing direction of the measuring person and an operating direction thereof are eliminated, so that the operationality of the alignment can be further improved.

According to this embodiment; the position of the measurement unit 3 with respect to the position of the eye to be examined "A" are adjusted using the real image resulting from the scattered light of the laser beam on the cornea in addition to the first and second virtual images. Therefore, the positional adjustment is performed from the three directions, so that it is possible to perform the alignment having further high precision. Thus, the measurement can be performed with further high reproducibility.

In this embodiment, the display of the image obtained from one of the CCDs 13 and 18 on the monitor 4, is performed corresponding to the on-and-off operation of one of the infrared LEDs 11 and 14, so that the operation related to the switching of screen display is simplified. A time required for such operation is shortened by the simplification, and a displacement of a position of the eye to be examined, which is caused during such operation is suppressed. Therefore, as described above, the measurement can be easily performed with high reproducibility.

According to this embodiment, the light which is irradiated from the oblique direction and reflected or scattered on the eye to be examined "A" is split into two in the direction to the CCD 18 and the direction to the high sensitive light receiving element 26 by the half mirror 16. Therefore, the light that travels from the eye to be examined "A" to the high sensitive light receiving element 26 is observed by the CCD 18. Thus, the measuring apparatus can be constructed with a size equal to the size of a conventional measuring apparatus. In addition, light equal to the light received by the high sensitive light receiving element 26 at the time of the measurement is observed by the CCD 18. Therefore, the alignment (Alignment 2) is performed from the oblique direction with a state close to the reflection or the scattered on the eye to be examined "A" at the time of the measurement. Thus, the more preferable alignment can be performed with a state adapted for the measurement.

In this embodiment, the measurement result, the data related to the alignment, and the data related to the person to be examined and the eye to be examined are recorded in the main body memory 29 as being associated with one another. Therefore, the alignment condition and the previous measurement result can be entirely read out based on the state of the person to be examined, so that it is more effective in grasping the process of the eye to be examined and to perform the data arrangement and utilization.

In this embodiment, the measuring apparatus is connected with the personal computer 33, so that the measurement result, the data related to the alignment, and the like can be led to the outside of the measuring apparatus. Therefore, the measurement result of the eye to be examined, the alignment condition, and the information related to the process of the eye to be examined can be commonly used between a plurality of measuring persons. Thus, it is possible to perform the accurate measurement of the optical properties of the anterior ocular segment by any measuring person. In addition, the person to be examined can undergo the above-mentioned accurate measurement by a near ophthalmologist, so that the convenience of the person to be examined related to the measurement can be improved.

What is claimed is:

1. An apparatus for measuring an optical property of an anterior ocular segment of an eye of a person to be examined, which comprises a laser beam source that irradiates a laser beam to the anterior ocular segment of the eye to be examined from an oblique direction with respect to the eye to be examined, a light receiving unit that receives scattered light of the laser beam scattered in the anterior ocular segment and converts the scattered light into an electrical signal, and a calculation unit that calculates the optical property of the anterior ocular segment from the electrical signal, wherein the apparatus further comprises:

a first light source that irradiates light to the eye to be examined from a front side with respect to the eye to be examined;
a first photographing means for photographing the eye to be examined from the front side;
a second light source that irradiates light to the eye to be examined from a first oblique direction with respect to the eye to be examined;
a second photographing means for photographing the eye to be examined from a second oblique direction with respect to the eye to be examined;
a position adjustment means for relatively adjusting each of positions of, the laser beam source, the light receiving unit, the first and second light sources, and the first and second photographing means with respect to a position of the eye to be examined;
a display unit that displays images obtained by the first and second photographing means; and
a switching unit that switches an image signal transmitted from one of the first and second photographing means to the display unit in accordance with an on-and-off operation of one of the first and second light sources;
the on-and-off operation of one of the first light source and the second light source and display on the display unit, of an image obtained by one of the first photographing means and the second photographing means are performed corresponding to each other, and
the positions of the laser beam source and the light receiving unit are relatively adjusted with respect to the position of the eye to be examined based on a first virtual image and a second virtual image,
the first virtual image is observed on an image of the eye to be examined, which is obtained by the first photographing means upon irradiation of the light from the first light source, and the second virtual image is observed on an image of the eye to be examined, which is obtained by the second photographing means upon irradiation of the light from the second light source,
the display unit displays each of suitable positions of the first virtual image and the second virtual image.

2. The apparatus for measuring an anterior ocular segment according to claim 1, wherein the switching unit switches a display of the suitable position of one of the first virtual image and the second virtual image in accordance with the on-and-off operation of one of the first and second light sources.

3. An apparatus for measuring an optical property of an anterior ocular segment of an eye of a person to be examined, which comprises a laser beam source that irradiates a laser beam to the anterior ocular segment of the eye to be examined from an oblique direction with respect to the eye to be examined, a light receiving unit that receives scattered light of the laser beam scattered in the anterior ocular segment and converts the scattered light into an electrical signal, and a calculation unit that calculates the optical property of the anterior ocular segment from the electrical signal, wherein the apparatus further comprises:

a first light source that irradiates light to the eye to be examined from a front side with respect to the eye to be examined;
a first photographing means for photographing the eye to be examined from the front side;
a second light source that irradiates light to the eye to be examined from a first oblique direction with respect to the eye to be examined;
a second photographing means for photographing the eye to be examined from a second oblique direction with respect to the eye to be examined;
a position adjustment means for relatively adjusting each of positions of, the laser beam source, the light receiving unit, the first and second light sources, and the first and second photographing means with respect to a position of the eye to be examined;
a display unit that displays images obtained by the first and second photographing means; and
a switching unit that switches an image signal transmitted from one of the first and second photographing means to the display unit in accordance with an on-and-off operation of one of the first and second light sources;
the on-and-off operation of one of the first light source and the second light source and display on the display unit, of an image obtained by one of the first photographing means and the second photographing means are performed corresponding to each other, and
the positions of the laser beam source and the light receiving unit are relatively adjusted with respect to the position of the eye to be examined based on a first virtual image and a second virtual image,
the first virtual image is observed on an image of the eye to be examined, which is obtained by the first photographing means upon irradiation of the light from the first light source, and the second virtual image is observed on an image of the eye to be examined, which is obtained by the second photographing means upon irradiation of the light from the second light source,
the second photographing means photographs a real image produced by scattered light at a time when the eye to be examined is irradiated with a laser beam from the laser beam source,
the switching unit switches the image signal transmitted from one of the first and second photographing means to the display unit in accordance with one of an on-and-off operation of the first light source and on-and-off operations of the second light sources and the laser beam source,
one of an on-and-off operation of the first light source and on-and-off operations of the second light sources and the laser beam source, and display on the display unit, of the image obtained by one of the first photographing means and the second photographing means are performed corresponding to each other, and
the positions of the laser beam source and the light receiving unit are relatively adjusted with respect to the position of the eye to be examined based on the real image, and the display unit further displays a suitable position of the real image.

4. The apparatus for measuring an anterior ocular segment according to claim 3, wherein the switching unit switches a display of: the suitable position of the first virtual image, and suitable positions of the second virtual image and the real image, in accordance with the on-and-off operation of one of the first and second light sources.

* * * * *

UNITED STATES PATENT AND TRADEMARK OFFICE
CERTIFICATE OF CORRECTION

PATENT NO. : 7,293,874 B2  Page 1 of 1
APPLICATION NO. : 10/850313
DATED : November 13, 2007
INVENTOR(S) : Suzuki et al.

It is certified that error appears in the above-identified patent and that said Letters Patent is hereby corrected as shown below:

On the Title Page, in column 2, under Abstract, line 7 of the abstract, after "fixed" insert -- on --.

On the Title Page, in column 2, under Abstract, line 10, delete "east" and insert -- easy --, therefor.

Column 3, line 21, delete "high-reproducibility" and insert -- high reproducibility --, therefor.

Column 3, line 33, delete "the" and insert -- The --, therefor.

Column 13, line 25, delete "CCD13" and insert -- CCD 13 --, therefor.

Signed and Sealed this

Second Day of September, 2008

JON W. DUDAS
*Director of the United States Patent and Trademark Office*